United States Patent [19]

Rabischong et al.

[11] 4,169,467
[45] Oct. 2, 1979

[54] ORTHOPAEDIC APPLIANCE FOR ENABLING PARALYTICS TO STAND ERECT

[75] Inventors: Pierre Rabischong, Saussan; Jean-Pierre Bel, Montpellier, both of France

[73] Assignee: Institut National de la Sante et de la Recherche Medicale - I.N.S.E.R.M., Paris, France

[21] Appl. No.: 817,502

[22] Filed: Jul. 20, 1977

[30] Foreign Application Priority Data

Jul. 23, 1976 [FR] France .................................. 76 23513
May 13, 1977 [FR] France .................................. 77 15465

[51] Int. Cl.² .............................................. A61F 5/04
[52] U.S. Cl. ................................ 128/80 G; 128/89 R; 128/DIG. 20
[58] Field of Search ................. 128/80 R, 80 G, 89 R, 128/87, 83, DIG. 20, DIG. 15

[56] References Cited

U.S. PATENT DOCUMENTS

| | | | |
|---|---|---|---|
| 3,867,930 | 2/1975 | Brown | 128/83 |
| 3,933,150 | 1/1976 | Kaplan et al. | 128/DIG. 15 |
| 3,993,056 | 11/1976 | Rabischong et al. | 128/89 R |
| 4,013,069 | 3/1977 | Hasty | 128/DIG. 20 |

*Primary Examiner*—John D. Yasko
*Attorney, Agent, or Firm*—Lewis H. Eslinger

[57] ABSTRACT

An orthopaedic appliance which enables paralytics to stand erect has a plurality of separate pieces of clothing to be fitted around body parts located between joints, the pieces having an inflatable support structure in the form of vertical tubes, and including belts formed of two strips of cloth fastened to opposite sides of the support structure, and devices inter-connecting pieces of clothing located on opposite sides of a body joint in the form of two rows of pins attached to the inflatable structures of the pieces of clothing and a mechanical articulation interconnecting the rows of pins. The inflatable tubes have generally rectangular cross-sections and the widths of the tubes of each support structure decrease symmetrically from the center to the side edges of the structure. The supporting devices connecting pieces of clothing on opposite sides of the hip joint have one row of pins detachably connected to the mechanical articulation.

8 Claims, 9 Drawing Figures

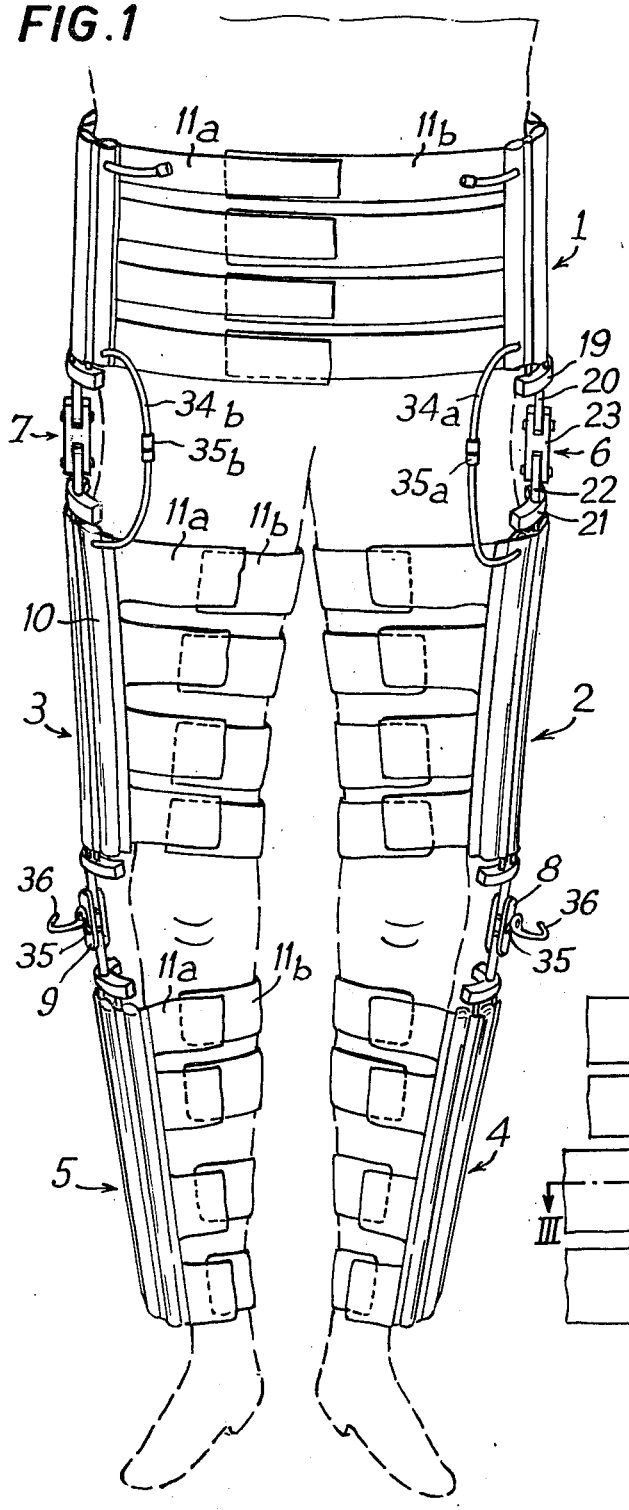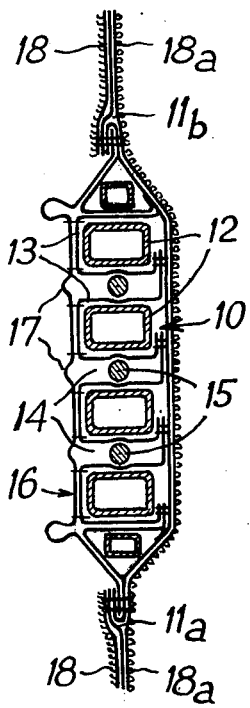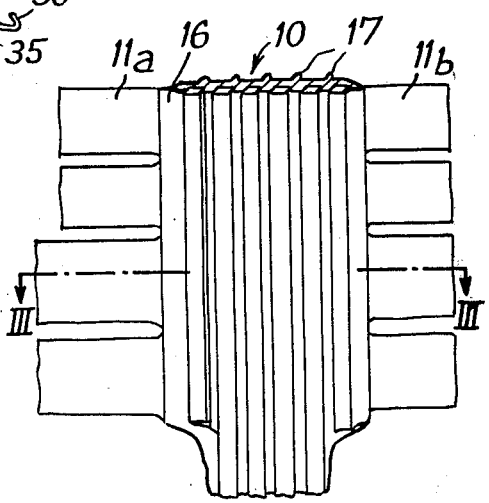

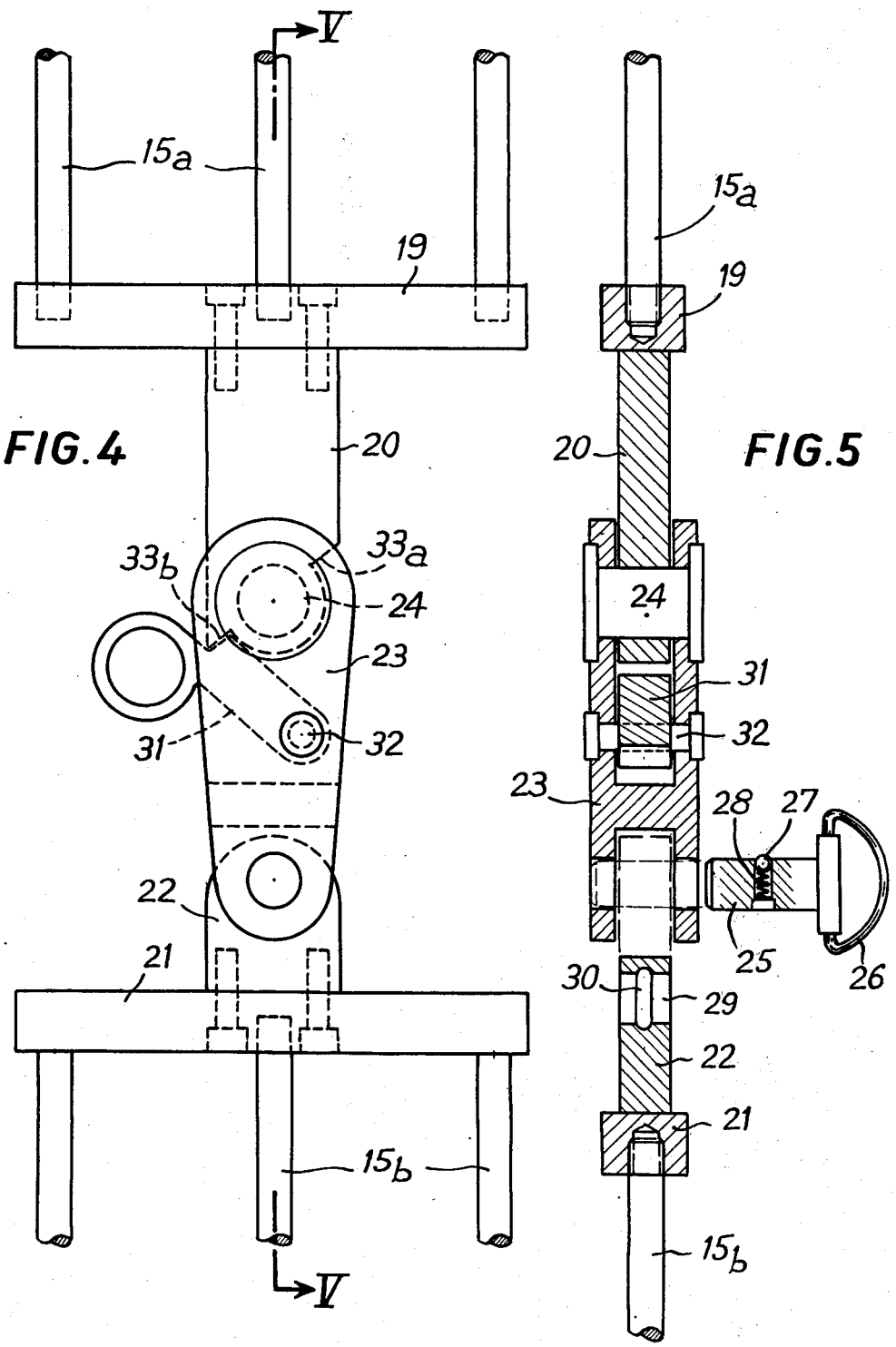

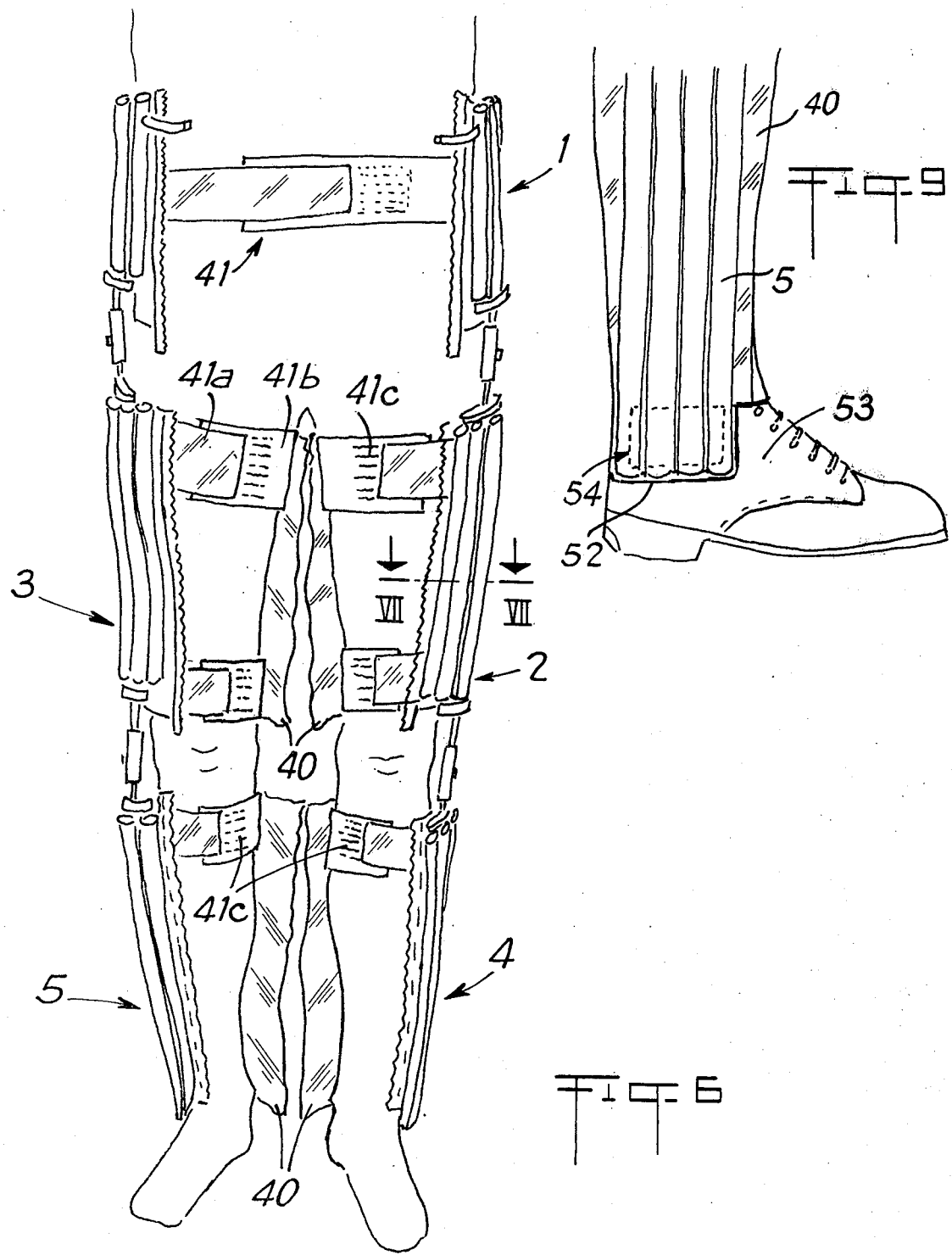

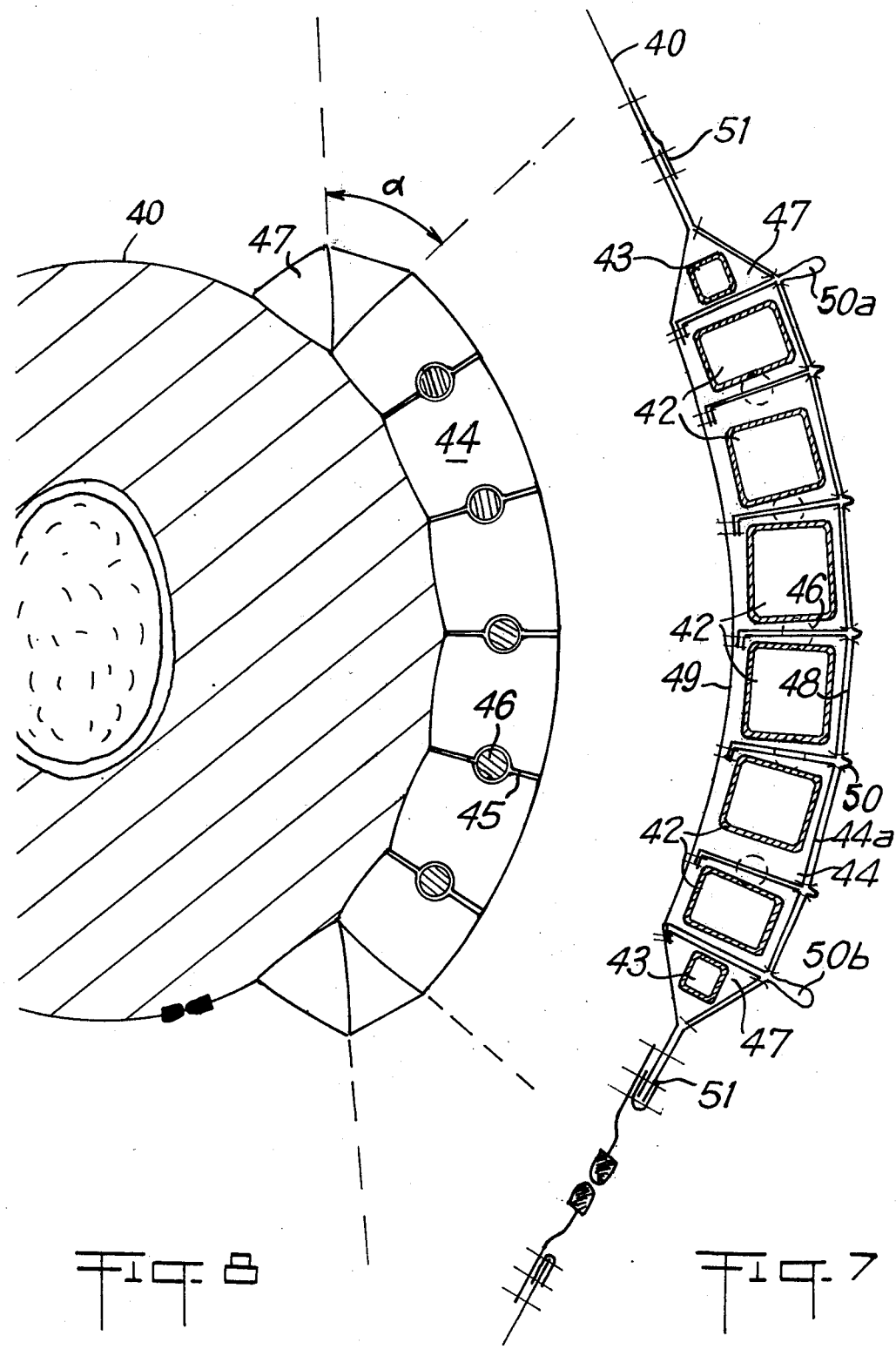

ORTHOPAEDIC APPLIANCE FOR ENABLING PARALYTICS TO STAND ERECT

This invention relates to orthopaedic appliances for enabling paralytics to stand erect and more particularly to an orthopaedic appliance comprising a plurality of separate pieces of clothing adjustably positionable around two respective body parts located between two joints of a paralysed person, each piece of clothing having an outer side portion arranged to be disposed against the outer side of the body part around which the piece of clothing is to be fitted, structures including a plurality of inflatable flexible tubes attached to the pieces of clothing to extend vertically over the outer side portions thereof, mechanical supporting devices connecting together vertically adjacent pieces of clothing located on opposite sides of a body joint in use of the appliance, each mechanical device including two rows of pins connected together by a mechanical articulation and attached to respective inflatable tube structures attached to the pieces of clothing connected together by the mechanical support device.

For each of the above known appliances it is necessary to manufacture six pieces of clothing equipped with inflatable structures, referred to herein as support modules. The six modules are: two modules for the right and left lower leg; two modules for the right and left thighs; one abdominal belt module and one module acting as a corset. Each module must be manufactured in several sizes which differ in perimeter and in height to be suitable for different people. The large number of different modules increases the cost of manufacture and necessitates in each appliance centre a large stock of modules in order to cater for all the sizes.

The mechanical support devices do not pose any particular problem because it is possible to change the length of the rods or spikes in order to adapt them to the different sizes.

One aim of the present invention is to reduce the number of support modules which need to be stocked by an appliance centre and in accordance with one aspect the invention provides an orthopaedic appliance as initially described wherein each piece of clothing includes at least one belt comprising a pair of strips of unstretchable material fastened by their first ends to the inflatable tube structure attached to the pieces of clothing, the strips being attached at the same height and on opposite sides of the inflatable tube structure, and means for connecting together the free second ends of the strips after they have been wrapped round the body part to which the piece of clothing is intended to be fitted.

With this construction the pieces of clothing have adjustable perimeters so that only modules of differing height need be provided.

In addition the orthopaedic appliance can be easy to put on and take off so that a handicapped person can carry out these operations alone.

The pieces of clothing may be suitable both for a right limb and for a left limb. The length of the strips is preferably calculated to be suitable for the largest perimeters, so that by making the overlap of the strips on one another vary, they can be adapted to any limb size. A portion of the length of the strips can easily be cut off if they are too long.

It is possible to make a complete appliance with only two different types of pieces of clothing, which enables manufacture to be standardized and stocks in appliance centres to be considerably reduced. Velcro-type fastenings offer a tensile strength of the order of 1 daN/cm$^2$, which is ample for keeping the modules firmly adjusted to the body and for transmitting the weight of the body to the mechanical supporting devices.

Another advantage of the appliances in accordance with the invention lies in the fact that they economize the efforts of handicapped persons in putting them on and taking them off.

A further advantage is that the strips can be separated from one another by free spaces and the appliance is therefore more ventilated and less disagreeable to wear.

Prior known appliances include slide fasteners. In order to put them on, the user must first of all put the pieces of clothing on a bed and then get up from his armchair and stretch out on the bed on top of the spread out pieces of clothing and fold them back round his body. But the majority of handicapped persons have a very weak abdominal muscular system and they cannot on their own engage the separable units of the slide fasteners. Hence they cannot get dressed or undressed on their own. The modules in accordance with the invention offer the advantage of eliminating this constraint. The handicapped person can by himself wrap the pairs of strips round his body and unfasten them while remaining seated in his armchair. Thus he can by himself put on an orthesis on condition that it can be uncoupled at the level of the corset.

According to a second aspect, the invention provides an orthopaedic device as initially described in which the supporting devices connecting the pieces of clothing located on opposite sides of the hip joint each have one row of pins detachably connected to the mechanical articulation thereof.

In accordance with a third aspect the invention provides an orthopaedic appliance as initially described wherein the inflatable tubes have cross-sections of generally rectangular configuration and the widths of said tubes decrease symmetrically from the centre towards the opposite side edges of each structure.

Some embodiments of the invention will now be described in more detail, by way of example, with reference to the accompanying drawings, in which:

FIG. 1 is a general front view of an orthopaedic appliance in accordance with the invention;

FIG. 2 is a partial elevation of a module of the appliance shown in FIG. 1;

FIG. 3 is a section along the line III—III of FIG. 2;

FIG. 4 is a front view of a mechanical articulation;

FIG. 5 is a section taken along the line V—V of FIG. 4;

FIG. 6 is a general view of another appliance in accordance with the invention, shown with the clothing partially cut away;

FIGS. 7 and 8 are horizontal sections along the line VII—VII of FIG. 6; and

FIG. 9 is a partial side view of the bottom end of the appliance of FIG. 6.

FIG. 1 represents an orthopaedic appliance being worn by a paralytic. This appliance includes five support modules: a module 1 which surrounds the pelvis, two modules 2 and 3 which surround the two thighs and two modules 4 and 5 which surround the lower legs. It includes besides, mechanical supporting devices or modules 6, 7, 8 and 9 which include each of them an articulation located respectively at the level of the hip and knee joints.

FIGS. 2 and 3 represent in elevation and in section a support module. It includes on the one hand an inflatable structure 10 and on the other hand pairs of strips 11 of unstretchable cloth fastened on opposite sides of the structure 10.

The structures 10 are composed of inflatable tubes 12 of square section. Each tube is enclosed in a cloth sheath 13. The sheaths 13 define between them passages 14, open at both ends, into each one of which a spike 15 which forms part of a mechanical supporting module engages. The assembly of the sheaths is enclosed inside a common cloth envelope 16 which includes gussets 17 on the outer face to enable the structures to follow the curvature of the body.

In previous ortheses the inflatable structure 10 was stitched onto the side of a piece of clothing which was fitted to one portion of the body of the patient.

In the illustrated orthesis instead of pieces of clothing pairs of strips of unstretchable cloth, for example, four pairs, as shown, each pair including two strips 11a, 11b, are fastened to the envelope 16 so that these strips form belts which can be wrapped round a portion of the body. On the inner face of each strip, that is to say, the face which is in contact with the body, is fastened a ribbon of a Velcro-type fastener, preferably the ribbon known as velvet, that is to say, the ribbon with eyes 18a. On the outer face of each strip is fastened a ribbon of a Velcro fastener with hooks 18. These ribbons extend along the whole length of the strips.

When the two strips of one pair have been wrapped round the body the two ends overlap and the ribbons with hooks and eyes are placed in contact with one another and hook together.

It will be observed that it would be sufficient to equip the outer side of only one strip of each pair with a ribbon with hooks and the inside of the other with a ribbon with eyes for obtaining fastening of the two strips. However, the fact of equipping both sides of each strip with Velcro ribbons enables manufacture of the support modules to be standardized.

Of course the Velcro-type fasteners might be replaced by equivalent fasteners distributed over the whole length, for example, by press-studs.

Because the Velcro fasteners exist over the whole length of the strips, the strips adapt themselves to any perimeter so that in order to obtain appliances which suit every size it is sufficient to make up a series of modules which differ only in their height.

The same modules serve for the left side and for the right side. Thus the modules 2 and 3 are identical, as are modules 4 and 5.

The pelvis module 1 may be composed of two thigh modules connected together by the strips. Thus an appliance as in FIG. 1 is composed on the one hand of two identical modules 4 and 5 which surround the lower leg and which include at their bottom end means of connecting them to the footwear and on the other hand of four other identical modules which surround respectively the thighs and the pelvis.

One important advantage of the support modules including strips and Velcro fasteners lies in the fact that a paralytic can put on these modules all alone while sitting in an armchair.

As shown in FIG. 3 the Velcro ribbons 18a are fastened to the inner face of the envelope 16 of the structure 10 so that the Velcro ribbon 18 of one of the two strips can come and hook itself on underneath the structure, which enables the support structure to be worn by a very thin person.

FIGS. 4 and 5 represent on a larger scale a preferred form of mechanical supporting module for the supporting modules designated 6 and 7 in FIG. 1. The module consists of a mechanical articulation including an upper row of pins or spikes 15a which are engaged in the sheaths 14 in the inflatable structure of the module 1. These spikes are fastened by their bottom ends to a curved plate 19 which bears against the hip. A top arm 20 is fastened to the plate 19.

The module includes a lower row of spikes 15b which are engaged in the sheaths 14 in the inflatable structure of one of the thigh modules 2, 3. The spikes 15b are fastened by their top ends to a curved plate 21 which bears against the top of the thigh. A bottom arm 22 is fastened to the plate 21.

The mechanical articulation includes a head 23 in the form of a double fork. The top fork carries an irremovable pin 24 about which the top arm 20 is pivoted and which is located at the level of the hip joint.

The bottom arm 22 is hinged about a removable pin 25 which is equipped with a loop 26 which can be folded down and which enables the pin to be pulled out. The pin 25 has a crossbore in which is located a retractable ball 27 loaded by a spring 28. The arm 22 includes a bore 29 through which passes the pin 25. An internal groove 30 is provided in the bore 29 and the ball 27 is urged into the groove 30 by the spring to keep the pin 25 in place. However, by pulling on the loop 26 the ball may be forced back into the crossbore and the pin 25 withdrawn. This enables a handicapped person to separate the articulation into two portions, and hence to put the pelvic module and the thigh modules on separately and then to couple them by means of the removable pins 25.

The articulations include in addition a latch 31 which enables the articulation to be locked in a certain position, for example, in the standing up position. The latch 31 is mounted on a third pin 32 parallel with the pins 24 and 25, which is likewise carried by the head 23. The top arm 20 includes shoulders 33a and 33b which abut against the latch when it is engaged to limit the angle of pivot of the arm 20 with respect to the head.

It may be seen in FIG. 1 that the inflatable structure of the support module 1 is connected to the inflatable structures of the modules 2 and 3 by tubes 34a, 34b furnished with rapid couplings 35a, 35b which enable the handicapped person to separate the portion of the appliance placed round the pelvis entirely from the lower portion placed round the legs.

The articulations at the knees likewise include latches 35. In order to facilitate unlocking of the latches to enable a wearer of the appliance to sit down without having to bend down to release the latches 35 manually, the latches are provided with operating handles having a rod ending in the form of a hook 36 (FIG. 1) which is arranged to bear against a chair to unlock the latches 35 automatically when the handicapped person sits down in the chair.

FIG. 6 shows an embodiment in which the front portions of the pieces of clothing 40 are partially cut away. Belts 41 are fastened to the inner walls of the pieces of clothing 40 at the ends of the latter. Each belt is formed of two strips of cloth 41a, 41b each carrying one half of a rapid fastener device, preferably of the Velcro-type 41c.

The belts 41 enable the appliance to be positioned quickly on a handicapped person before the pieces of clothing 40 are firmly attached to the body by means of lace or slide fasteners (not shown). Being located at the ends of the pieces of clothing 40, next to the articulations, the belts 41 ensure reinforcement of the clothing 40 by taking up part of the tangential forces.

The inflatable structure shown unwrapped and wrapped around a limb in FIGS. 7 and 8, respectively, is designed to form a rigid structure which will cover about a third of the surface of a limb and distribute over it the high stresses due to motorization, without compressing the limb in the manner of a tourniquet.

The structure includes a series of parallel, inflatable tubes 42. The cross-section of the tubes when deflated is generally rectangular, this term being taken in the broad sense and including a square shape and having the corners rounded off. This shape facilitates manufacture of the moulds and removal of the tubes from the mould.

Advantageously the widths of the tubes decrease symmetrically with respect to the axis of the structure in going from the centre towards the two edges of the structure. As may be clearly seen in FIG. 7, the two side tubes 43 have a rectangular or square section distinctly smaller than the other tubes.

The tubes 42 are placed in closed sheaths 44 of cloth, which define between them pockets 45, open at both ends, into some of which spikes 46 of the mechanical supporting devices are inserted. The spikes 46 may have a circular or semi-circular cross-section. They may be made of metal, such as steel, or of stratified resin, preferably of resin reinforced with carbon fibres so that they have a low weight but the necessary mechanical strength.

The sheaths 44 exhibit a trapezoidal section the wide base 44a of which is located on the outside.

Each of the side tubes 43 is placed inside a closed cloth sheath 47 of triangular cross-section. The assembly of the tubes 42, 43 and the sheaths 44 and 47 is enclosed in a common envelope of cloth, composed of an outer wall 48 and an inner wall 49 which is fastened by peripheral stitching 51 to the piece of clothing 40.

The outer wall 48 includes vertical undulations 50 which constitute deformable gussets and which are located in prolongation of each of the ducts 45.

The two gussets 50a and 50b located between each of the triangular sheaths 47 and the adjoining sheath have a much greater width than that of the other gussets, so that the sheaths 47 can pivot by an angle α which may vary between 10° and 60°, as shown in FIG. 8. Thanks to this pivoting the sheaths 47 can lie with one side against the limb and follow the curvature of the limb without creating a hard point along the inflatable structure which could be very painful.

By employing gussets 50 and sheaths 44, 47 of different dimensions, structures can be made up which are more enveloping, but do not compress the limbs.

FIG. 9 represents the bottom end of one of the pieces of clothing 40 which is wrapped around the ankle and of the inflatable structure 5 fastened to it. The structure 5 includes a downward extension 52 which protrudes beyond the bottom end of the piece of clothing and covers over the leg of the footwear 53. The extension has on its inside face one half 54 of a Velcro-type fastener. The leg of the footwear includes on its outer face the other half of the fastener. Assembly of the two halves of the fastener 54 borne by the structure and by the footwear enable the clothing to be connected to the footwear and constitutes a reference of level for dressing the paralysed person, as well as relieving the ankles of the paralysed person by carrying forward directly onto the footwear a portion of the vertical forces.

We claim:

1. An orthopaedic appliance for enabling paralytics to stand erect, comprising a plurality of separate pieces of clothing respectively adjustably positionable around the pelvis, thighs and calves of a paralyzed person and each piece having at least one outer side portion which in use of the appliance encloses the outer side of its respective body part, and six support modules associated with said clothing pieces including a first pair of modules enveloping the calves of the wearer, and four identical modules two of which envelope the wearer's thighs and two of which envelop the wearer's pelvis, said modules each comprising an inflatable structure having two vertical side edges and including a plurality of parallel, flexible and inflatable tubes attached to its associated clothing piece to extend substantially vertically over the outer portion thereof, said modules being located in generally vertical alignment on opposite sides of the wearer's body when in use with the modules enveloping the pelvis being located above the hip joints and the modules enveloping the thighs being between the hip joints and the knee joints; and mechanical support devices associated with each of said modules for connecting together vertically adjacent pieces of clothing in the appliance, said mechanical support devices comprising at least two rows of rigid pins and a mechanical articulation interconnecting said rows of pins and arranged to be located at the level of the body joint between adjacent pieces of clothing, and means for attaching said rows of pins to respective inflatable structures of their associated pieces of clothing, said modules each including a plurality of connecting belts each of which comprises a pair of strips of unstretchable material attached to the respective side edges of the inflatable structure of their associated module at the same height; one of said pair of strips including an eye-ribbon of a Velcro-type fastener on its inner face directed inwardly towards the body of the paralytic and the other of the strips carrying a hook-ribbon of a Velcro-type fastener on its outer face.

2. In an orthopaedic appliance for enabling paralytics to stand erect, comprising a plurality of separate pieces of clothing each adjustably positionable around a body part located between two joints of a paralyzed person and each piece having an outer side portion which in use of the appliance encloses the outer side of the body part, an inflatable structure on each piece of clothing having vertical side edges and including a plurality of parallel, flexible and inflatable tubes attached to said garment piece to extend substantially vertically over the said outer portion thereof, pairs of adjacent ones of said pieces of clothing being located on opposite sides of a body joint, in use of the appliance, a mechanical support device connecting together the pieces of clothing of each said pair of adjacent pieces, said device comprising two rows of rigid pins and a mechanical articulation interconnecting said rows of pins and arranged to be located at the level of the said body joint, and means for attaching said rows of pins to respective inflatable structures of said pair of adjacent pieces of clothing located on opposite sides of the said joint, the improvement which comprises said inflatable tubes having generally rectangular cross-sections and the widths of said tubes in each said structure decreasing from the centre towards the vertical side edges of said structure symmetrically on each side of said structure; each of said tubes being placed inside a closed sheath of cloth, the sheaths defining between them pockets having open ends, pins of said mechanical support devices being inserted into at least some of said pockets, each said inflatable structure including two lateral sheaths, inflatable tubes extending along said side edges of said structure located within said lateral sheaths, said lateral sheaths having a cross-section of generally triangular shape, and sheaths which contain other tubes of said structure, said latter sheaths having a cross-section of generally trapezoidal shape with the wide base thereof directed towards the outer side of the structure.

3. The improvement of claim 2, in which said cloth sheaths of each structure are placed inside a common cloth envelope, said envelope having an inner wall positioned against the body of the paralytic and an outer wall placed opposite said inner wall, said outer wall having vertical undulations in the form of deformable gussets located between the said cloth sheaths and said undulations located between said lateral sheaths and the sheath adjacent thereto being bigger than the other undulations.

4. In an orthopaedic appliance for enabling paralytics to stand erect, comprising a plurality of separate pieces of clothing each adjustably positionable around a body part located between two joints of a paralyzed person and each piece having an outer side portion which in use of the appliance encloses the outer side of the body part, an inflatable structure on each piece of clothing having vertical side edges and including a plurality of parallel, flexible and inflatable tubes attached to said garment piece to extend substantially vertically over the said outer portion thereof, pairs of adjacent ones of said pieces of clothing being located on opposite sides of a body joint, in use of the appliance, a mechanical support device connecting together the pieces of clothing of each said pair of adjacent pieces, said device comprising two rows of rigid pins and a mechanical articulation interconnecting said rows of pins and arranged to be located at the level of the said body joint, and means for attaching said rows of pins to respective inflatable structures of said pair of adjacent pieces of clothing located on opposite sides of the said joint, the improvement which comprises said inflatable tubes having generally rectangular cross-sections and the widths of said tubes in each said structure decreasing from the centre towards the vertical side edges of said structure symmetrically on each side of said structure; two of the inflatable structures of said pieces of clothing being located to envelop the ankles of a paralytic and including a downward extension which covers over a leg part of the paralytic's footwear, said extension having an inside face which is located against the leg of the footwear, and a Velcro-type fastener portion with hooks and eyes on said inside face for cooperation with a second fastener portion of the same type fastened to the outer face of the leg of the footwear.

5. In an orthopaedic appliance for enabling paralytics to stand erect, comprising a plurality of separate pieces of clothing each adjustably positionable around a body part located between two joints of a paralysed person and each piece having an outer side portion which in use of the appliance encloses the outer side of the body part, an inflatable structure on each piece of clothing including a plurality of parallel, flexible and inflatable tubes attached to said garment piece to extend substantially vertically over the said outer portion thereof, pairs of adjacent ones of said pieces of clothing being located on opposite sides of a body joint, in use of the appliance, a mechanical support device connecting together the pieces of clothing of each said pair of adjacent pieces, said device comprising two rows of rigid pins and a mechanical articulation interconnecting said rows of pins and arranged to be located at the level of the said body joint, and means for attaching said rows of pins to respective inflatable structures of said pair of adjacent pieces of clothing located on opposite sides of the said joint, the improvement which comprises the supporting devices connecting the pieces of clothing located on opposite sides of the hip joint each having one of said rows of pins connected detachably to said mechanical articulation.

6. The improvement of claim 5, in which said mechanical articulations of said supporting devices located at the level of the hip joint, each includes two arms fastened to respective ones of the said rows of pins, an intermediate head in the form of a double fork and two pins pivotally connecting said arms to said intermediate head, one of said pins being removable for detaching one of said arms from said intermediate head.

7. The improvement of claim 6, in which said removable pin includes a retractable ball, and said one arm has a pin receiving bore with a groove in which said ball engages.

8. The improvement of claim 6, in which said intermediate head carries a third pin parallel with said two pins, and a latch is pivoted on said third pin for locking said articulation in a predetermined position, said latch having an operating lever which is extended by a control rod so arranged that when the paralytic sits down in a chair said rod bears against the chair and causes said latch to pivot to unlock said articulation.

* * * * *